United States Patent [19]

Harrick

[11] Patent Number: 4,732,475
[45] Date of Patent: Mar. 22, 1988

[54] INTERNAL REFLECTION NANOSAMPLING SPECTROSCOPY

[76] Inventor: Nicolas J. Harrick, Croton Dam Rd., Ossining, N.Y. 10562

[21] Appl. No.: 889,238

[22] Filed: Jul. 25, 1986

[51] Int. Cl.$^4$ ............................................. G01N 21/01
[52] U.S. Cl. ..................................... 356/300; 356/244
[58] Field of Search ..................... 356/300, 244, 136

[56] References Cited

U.S. PATENT DOCUMENTS 3,415,602 12/1968 Harrick ............................... 356/256
3,540,025 11/1970 Levin et al. ......................... 356/136

OTHER PUBLICATIONS

Harrick, "Internal Reflection Spectroscopy", Interscience Publishers, 1967, pp. 124–125.

Primary Examiner—Vincent P. McGraw

[57] ABSTRACT

A novel internal reflection element and associated optics for examining micro- or nano-gram quantities of a sample material by internal reflection spectroscopy, wherein the element is sized for ease of handling, and is configured to allow entrance of a radiation beam at one end, to guide the radiation to the opposite end, to concentrate the guided radiation at a small triangular-shaped sampling surface, from which the beam is directed out of the element. Adjustable masking means is also provided to reduce the unmodulated content or undesired portions of the exiting beam.

12 Claims, 9 Drawing Figures

INTERNAL REFLECTION NANOSAMPLING SPECTROSCOPY

This invention relates to spectroscopy of minute samples, and in particular to internal reflection spectroscopy of microgram and nanogram sample sizes.

BACKGROUND OF THE INVENTION

Reference is made to my book entitled INTERNAL REFLECTION SPECTROSCOPY, published 1967 by Interscience Publishers. This book systematically describes theory, instrumentation and applications of internal reflection spectroscopy (IRS), whose contents are hereby incorporated by reference. Chapter 4 describes in detail various geometries of internal reflection elements (IRE), which essentially consist of a transparent optical element for the radiation involved having an entrance or first surface for receiving a focussed or collimated beam of incident radiation of an angle that allows the beam to enter the element and that causes the beam to become incident on a second or sampling surface containing the sample to be investigated at an angle exceeding the critical angle so that total reflection occurs and the resultant beam is caused to exit the element at a third surface and thereafter can be optically processed in a standard spectrometer. As is explained in the book, at the sampling surface the beam becomes modulated by interaction of its evanescent wave, usually by absorption, with the sample, so that when the modulation content of the existing beam is transformed into a curve of absorption as a function of beam wavelength, the usual absorption spectrum of the sample is obtained.

IRS has a number of advantages over other spectroscopy techniques. It can be used with liquid or solid samples and little or no sample preparation is required. This is especially important for very small samples, e.g., microgram and nanogram quantities, for which there is currently very wide interest. Whenever the internal reflection method can be used to obtain an effective pathlength greater than the actual thickness of a (film) sample, then an improvement in spectral contrast, thus sensitivity, is achieved relative to simple transmission. Under appropriate conditions, this increase in sensitivity may be as high as ten. Another important advantage of IRS in micro- and nano-sampling applications is the ease with which samples are prepared and handled. It is only necessary to bring the sample in contact with or in close proximity to the sampling surface. For example, to record the spectrum of a fiber, one needs only to place the end of the fiber in contact with a suitable IRE to record its spectrum.

Because of the above-mentioned advantages, internal reflection is the preferred method for micro- and nano-sampling. In principle, such experiments could be done using a large prism (hemisphere) and diffraction limited optics, but there would exist the problems of locating the sample on the micron-size sensitive area. Hence, for such small samples, the IRE or prism size should be chosen to be comparable to that of the sample. However, such small prisms cannot be easily fabricated or handled. If larger prisms are used, means must be devised for masking the light beam to make its focus comparable to the size of the sample and finally to place the sample on the sampling surface at the exact location from which the small light beam is reflected. A further disadvantage of the larger prism is that the light beam is refracted as it enters the prism and the beam focus size is larger at the sampling surface; hence the light intensity and therefore sensitivity is reduced.

In my book I describe a technique for conducting investigations of minute samples. But the techniques described require multiple reflections at the sampling surface, with the result that only a small fraction of the radiation interacts with the sample and thus the degree of modulation of the exiting beam is extremely small making for poor spectra. Thus, the techniques described therein have not been completely satisfactory.

BRIEF DESCRIPTION OF INVENTION

The principal object of the invention is an IRE for use in IRS that enables the examination of minute samples, in the micro-or nano-gram range.

A further object of the invention is IRE sampling apparatus for examining minute samples and that can be used as an accessory in existing spectrometers.

These and further objects and advantages as will appear hereinafter are achieved with a novel IRE characterized by a size capable of being conveniently handled by a user, but possessing a novel configuration that combines within it the functions of a radiation or light guide and a radiation or light concentrator or funnel for concentrating the radiation at a small prism end where the sample can be conveniently located.

As a further feature of the invention, the novel IRE is combined with a masking element, which may be adjustable by the user, to restrict the radiation output to substantially that portion modulated as a result of interaction with the sample to increase sensitivity.

BRIEF DESCRIPTION OF DRAWINGS

One form of the novel apparatus of the invention will now be described in greater detail with reference to the annexed drawings in which.

DETAILED DESCRIPTION OF PREFERRED EMBODIMENT

Figure 1:
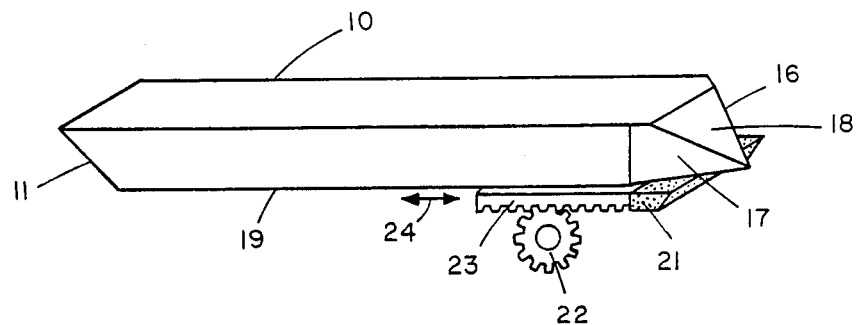
FIG. 1 is a perspective view of one form of the IRE of the invention.

FIG. 1 illustrates in perspective a view of one form of the novel IRE of the invention useful for examining or analyzing minute samples in IRS. The IRE 10 comprises an optically transparent element composed of any of the materials described in my above-reference book. For example, for infrared (IR) radiation, which is the most common, a typical material is zinc selenide (ZnSe). The element is, essentially, a plate-like element with polished surfaces having over most of its length a rectangular cross-section, and at one end a 45 degree bevelled surface 11 so that incident radiation 12 at the top left end surface portion, referenced 13, will totally reflect from the bevelled surface 11 and be propagated by multiple reflections through the main body of the element 10 toward the right end, shown schematically by the arrows 15. More accurately, the central rays travel parallel to the long surfaces while the diverging rays are reflected a few times from the surfaces and thus constrained to remain within the volume bounded by the four long surfaces and hence the beam remains focussed as it was at the entrance aperture 13. The right end of the plate 10 is tapered down to a point (the tapered portion is referenced 16) by polishing of the two opposite side 17 and top 18 surfaces. The bottom surface 19 remains flat. The result is a triangular surface 18 which acts as the sampling surface and which decreases in size from its base to its apex. It is also at a 45 degree angle and thus parallel to surface 11. The radiation which then totally reflects off of sampling surface 18 is thus directed downward as shown by arrow 20 and is incident on the bottom surface 19 at an angle that allows it to pass out of the element 10. The central ray will impinge orthogonally on surface 19 while the diverging rays will be at a small angle with respect to the normal to the surface.

A masking element 21 is mounted by means not shown below the bottom surface 19 of the IRE 10 and generally opposite to the sampling surface 18. The mask 21 is opaque to radiation and is provided with any convenient form of mechanism, a gear 22 and rack 23 is illustrated in FIG. 1, whereby the mask 21 can be moved by the user in the longitudinal direction of the IRE as illustrated by arrow 24. The function of mask 21 is to selectively block off radiation reflected from sampling surface 18 and not interacting with the sample.

Figure 2:
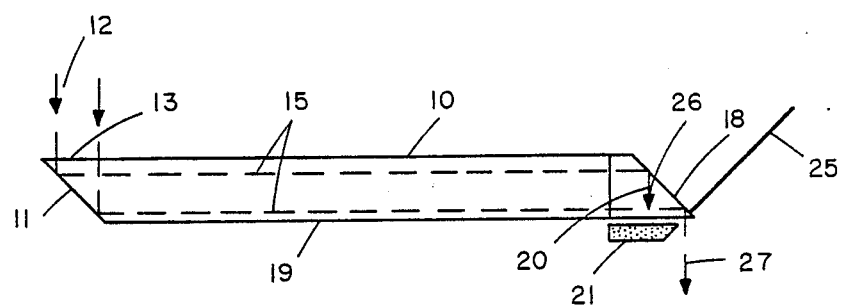
FIGS. 2 and 3 are side and top views, respectively, of the IRE of FIG. 1.
Figure 3:
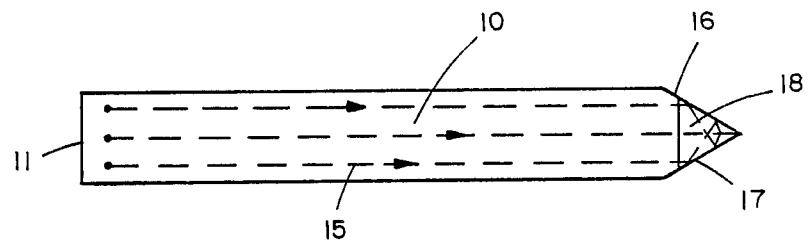

The light paths are illustrated in FIGS. 2-5. FIG. 2 illustrates the IRE of the invention being employed to obtain the absorption spectrum of a fiber. The fiber 25 is positioned at the tip of the triangular sampling surface 18, as depicted in FIG. 2. As will be observed, most of the radiation, illustrated by numeral 26, does not interact with sample fiber 25. Only a small fraction indicated by numeral 27 will contain information about the sample material 25. The mask 21 is positioned by the user to block or screen out substantially all non-interacting radiation 26, while allowing the absorption-modulated information 27 to exit from the apparatus of the invention. The user can determine the optimum position of the mask 21 by observing the output signal as he adjusts the longitudinal position of mask 21.

Figure 4:
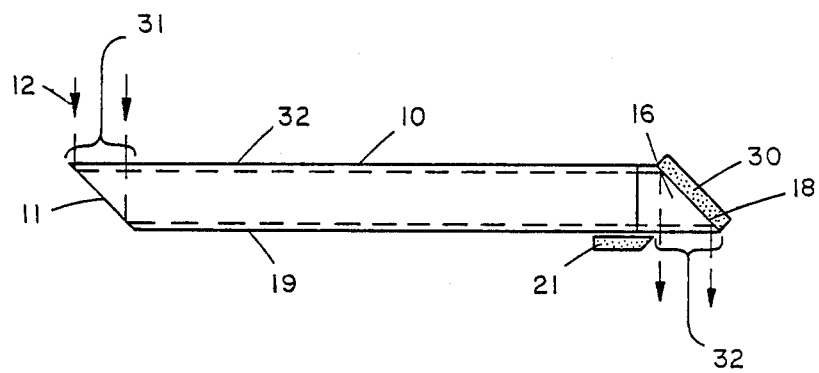
FIGS. 4 and 5 are views similar to FIGS. 2 and 3 in another application.
Figure 5:
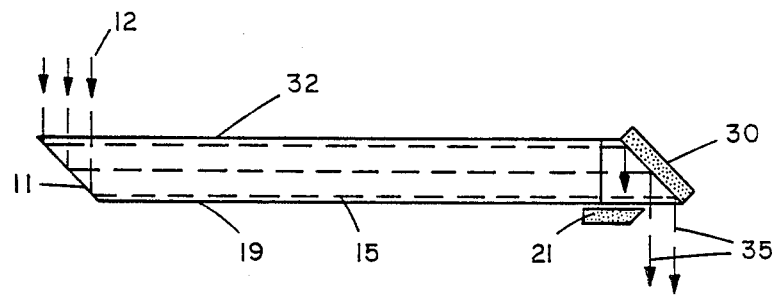

FIGS. 4 and 5 also illustrate the operation of the preferred form of IRE of the invention. FIG. 4 illustrates a larger sample 30 placed on the sampling surface 18. The entrance aperture for the IRE 10, designated 31, is that portion of the top surface 32 which lies opposite the bevelled surface surface 11. It will be appreciated that by reorienting the surface 11 so that it is at right angles to the top and bottom surfaces of the element 10, the radiation can be introduced at that right-angled end instead of at the surface portion 31. As a further alternative, the entrance aperture 31 can be located at the bottom surface, in which case the bevelled surface 11 would have to be reversed. In all three cases, the radiation fills the light guide portion of element 10. Also, to achieve the latter, bevel surface 11 need not be parallel to sampling surface 18, nor need the side and top and bottom surfaces be parallel. However, the arrangement as illustrated with the entrance aperture at top or bottom is preferred because the entrance aperture is larger and simplifies the transfer optics. With the mask 21 fully retracted, as shown in FIG. 4, substantially all of the input radiation, after concentration by the funnel 16, exits from the IRE over an exit aperture designated 32. FIG. 5 illustrates the situation where the user desires to limit his examination to the rightmost portion of the sample 30, in which case mask 21 is moved to the right allowing only that portion 35 of the radiation interacting with the rightmost and thus smallest portion of the sample to exit from the IRE via an exit aperture designated by the width of the two arrows 35.

As will be observed, the elongated light guide section of element 10 conducts the light from the entrance aperture 31 to the prism sampling surface 18 and allows the IRE to be of a size that is easily handled. The triangular prism 16 acts as a funnel for the light, yielding higher energy from the very small sampling area, and allows one to control, by means of the mechanical mask 21, the size of the active sampling area to a value smaller than about one mm in diameter, preferably from about one square millimeter down to micron dimensions.

An example of typical dimensions of the preferred IRE of the invention are as follows. The length of the top surface 32 is about 1 cm, width of about 1.5 mm and a depth of about 1 mm. Thus the entrance aperture 31 is about 1.5×1 mm. The length of the funnel prism is about 1.5 mm, resulting in an exit aperture of about 1.5×1 mm and a triangular sampling surface having a base of about 1 mm and a height to the apex of about 1 mm. As noted, the sample, liquid, solid, e.g., end of a fiber, is placed in contact with or in close proximity to the sampling surface 18. The sampling surface area is substantially matched to the sample size by adjusting the position of the mask 21. When the mask is fully retracted, the effective sampling area for the dimensions given is about one mm in diameter. As the mask 21 is moved to the right, it blocks light from the wider parts of the sampling surface which lie directly above the mask and the sampling area is reduced in this way. It is thus possible to reduce the effective sampling area diameter to, e.g., 20 microns near the tip or apex of the triangular area. The sides of the triangular area are polished and due to total reflection the structure acts as a funnel concentrating more light near the tip of the sampling surface.

Figure 6:
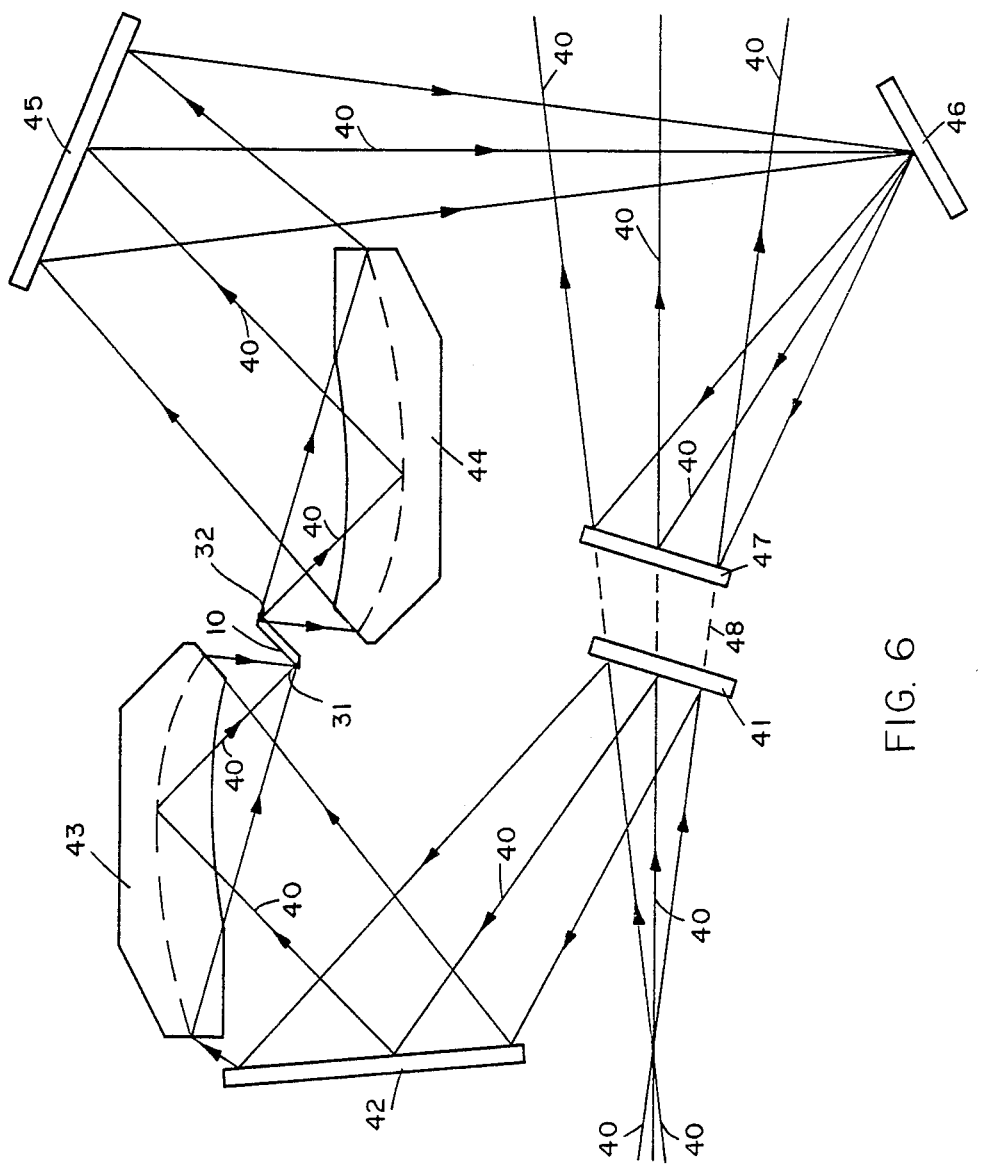
FIGS. 6 and 7 illustrate, respectively, several forms of transfer optics for bringing the radiation beam out of and back into a spectrometer after passage through the IRE of FIG. 1.
Figure 7:
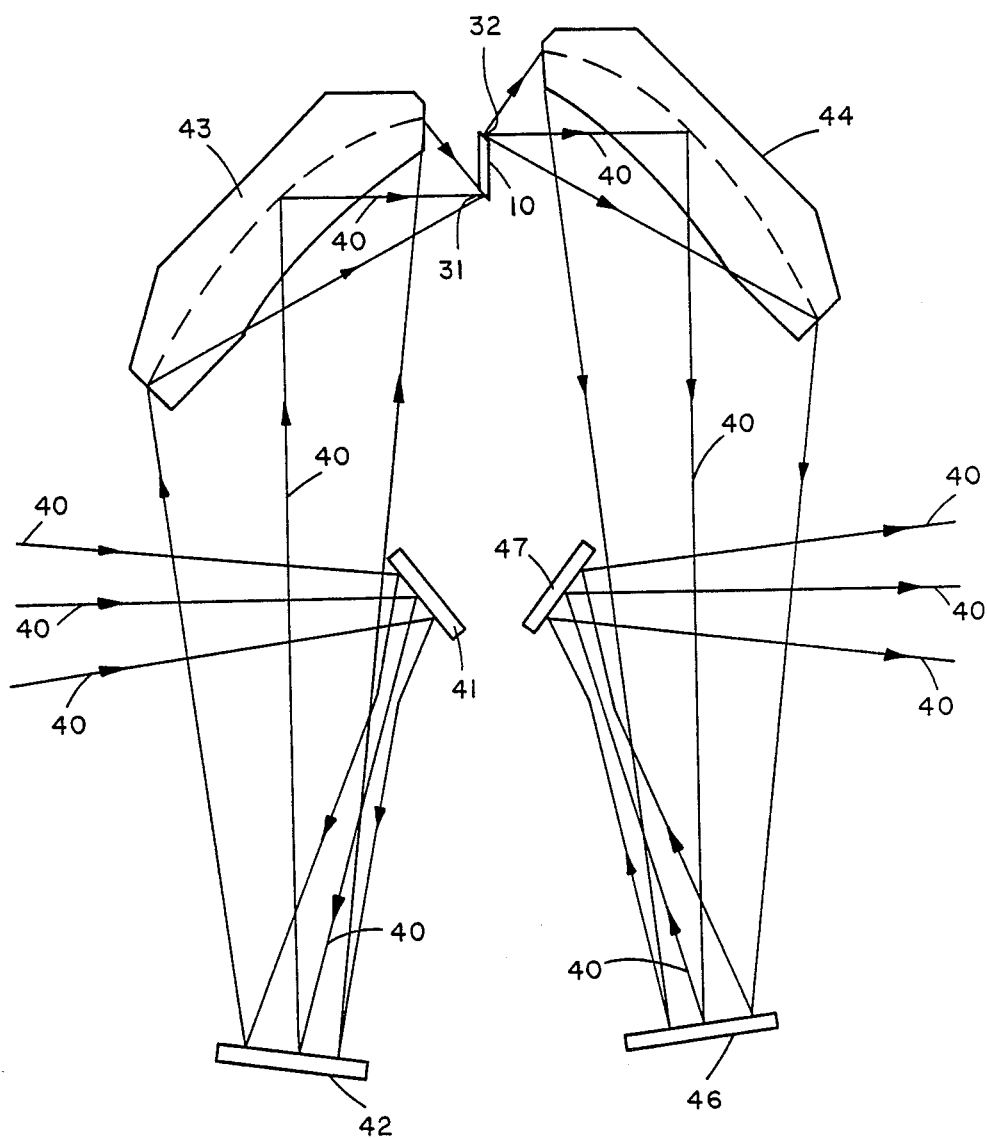

The IRE of the invention is adapted for use within the sampling chamber of conventional spectrometers, of the type generally described in my book, and also of the more modern types using Fourier analysis of the modulated beam. Suitable instruments are described in Chapter VI of my book. In the prior art IREs, which typically have dimensions of 5 cm long by 1 cm wide and 1 mm thick, numerous methods are available to use such IREs with conventional spectroscopic equipment. Because of the much smaller size of the IRE of the invention, special transfer optics are necessary which can be inserted in the sampling space of the spectrometer with little or no disturbance of the optical alignment, which will allow the radiation beam to be focussed down onto the entrance aperture 31 of the IRE and will allow the the exit beam to be returned to the spectrometer for processing of the signal obtained from the detected modulated radiation. The IRE of the invention can be located between the radiation source and the monochromator, or between the latter and the detector. Modifications of the layouts illustrated in Chapter VI of my book can be employed. Two examples of a suitable optical geometry are illustrated in FIGS. 6 and 7. An accessory or attachment for use with conventional spectrometers would thus incorporate conventional means (not shown but illustrated in my book) for supporting the reflectors illustrated in FIGS. 6 and 7 as well as the IRE 10 and the mask means (also not shown) for controlling the size of the sampling area. If desired, a microscope can also be provided in a position that allows the user to view the entrance and exit apertures of the IRE while adjusting the transfer optics.

In the geometry of FIG. 6, which uses side focus optics, the beam 40 reflects off of plane mirrors 41, 42 and is then incident on ellipsoidal mirror 43, which focusses the beam onto the entrance aperture 31 of IRE 10. After exiting, the beam 40 is focussed by ellipsoidal reflector 44 and plane mirrors 45, 46 and 47 back into the spectrometer. As indicated by dashed lines 48, the focussing parameters are retained and thus the accessory or attachment of the invention requires little or no change in the spectrophotometer. FIG. 7 illustrates a variation of FIG. 6 using center focus optics (the same reference numerals are used to reference similar elements), and plane mirrors 41, 42, 46, 47 and ellipsoidal mirrors 43, 44.

As will be observed, the preferred IRE of the invention is fixed angle, single pass, single reflection attachment. While the reasons for using variable angle, multiple pass, multiple reflection geometries stated in my book might be employed here, what is the more important consideration is that the output or exiting beam is restricted as much as possible substantially only to radiation which actually interacted with the minute sample, to ensure maximum sensitivity contrast in the resulting spectra. and thus the exemplary embodiment is preferred.

Figure 8:
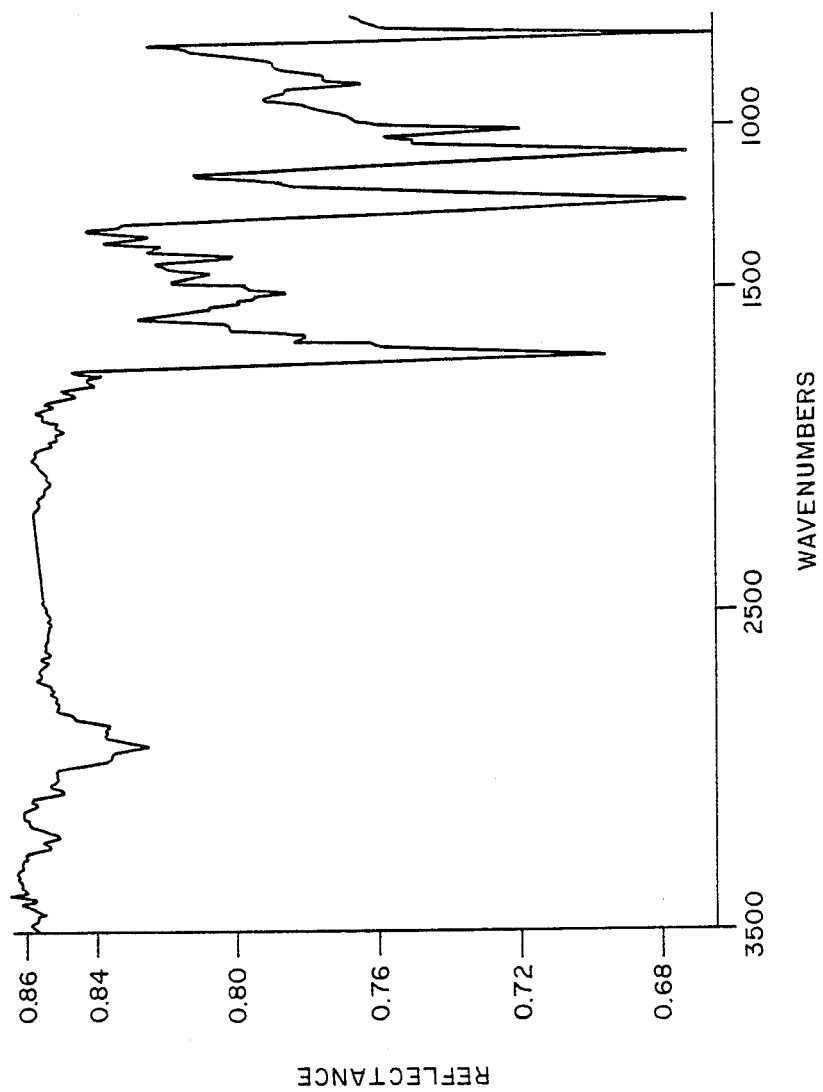
FIGS. 8 and 9 are sample spectra taken with the IRE of FIG. 1.
Figure 9:
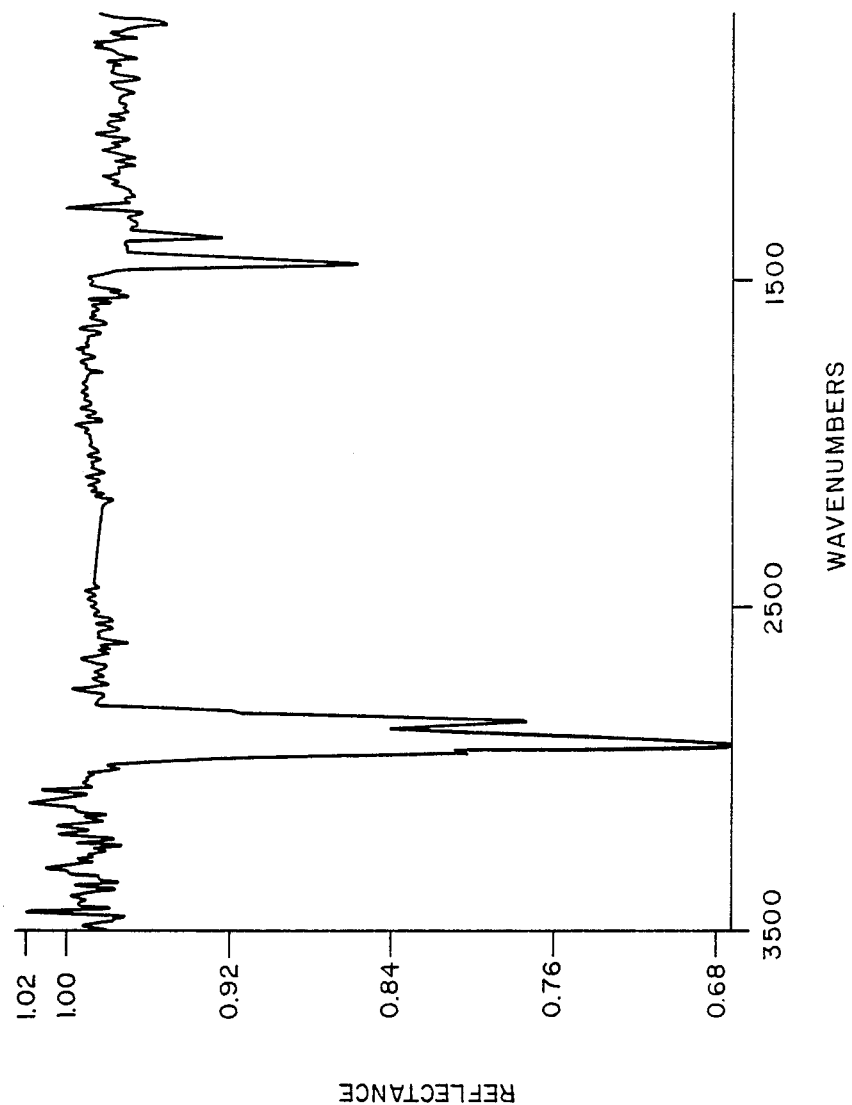

This is best illustrated in the spectra shown in FIGS. 8 and 9, which were obtained in a Model Sirius 100 Mattson spectrometer, in which the accessory of the invention using the transfer optics illustrated in FIG. 6 were mounted in the sampling chamber of the spectrometer. Both spectra show absorption as reduced reflectance from the sample surface in the infrared range as a function of wavelength or its inverse wavenumbers, using ZnSe as the material for the IRE element. The sample for the FIG. 8 spectrum was a polyethylene perephthalate (PET) fiber only 20 microns in diameter, whose end as shown in FIG. 2 was positioned on the sampling surface. Thus the spectrum of FIG. 8 was obtained from only one nanogram of the sample. As will be observed, the spectrum is excellent. The FIG. 9 spectrum was obtained with a tiny drop of paraffin oil in the sampling surface. Again, the spectrum is excellent.

As previously noted, the IRE element can be constructed of any of the materials mentioned in my book, and any of the radiation ranges, typically ultra-violet, visible, and infrared, likewise mentioned in my book with the appropriate transparent IRE material can similarly be employed, though most often the IR range provides the most useful information about the sample.

By choosing IRE dimensions which allow easy handling and mounting of this element, typically of the order of 10×1×1 mm, allowing the examining radiation to enter one prism end through the top surface as illustrated or the bottom surface or through the end 11 if another optical geometry were found more convenient, so that the the entering radiation fills the entrance aperture and is guided or propagates down the length of the continuous one-piece IRE body where the beam cannot expand and therefore cannot be diluted, then concentrating or funnelling the beam down to the smaller area sampling surface where it can interact with the sample before exiting from the element, in combination with the adjustable mask which restricts the exiting beam as much as possible to the desired sample-interacting beam portion, a remarkably high sensitivity output is obtained for micron- and nano-sized samples. When combined with the relative ease of sample handling, my invention should greatly expand the applications of the well established IRS to the investigation or analysis of a wide range of materials.

While the invention has been described in connection with preferred constructions and materials, it will be evident to those skilled in this art that the invention is not limited thereby, and application of the principles enunciated herein resulting in modifications thereof are well within the skill of those in this art and are intended to be part of my invention.

What is claimed is:

1. A single pass, single reflection, internal reflection element for use in internal reflection spectrometry comprising:
    (a) a radiation-transparent optical element having at one end a first surface for entry of a beam of radiation and having at another end a second surface smaller in area than the first surface for receiving a sample to be examined and having a third surface from which the radiation may exit, said optical element being configured in such manner that radiation entering the first surface will in a single pass be guided by multiple internal reflections to and concentrated to become incident once on the smaller second surface at an angle exceeding the critical angle such that it will become modulated by interaction with the sample and the resultant radiation after incidence once on the second surface directed toward the third surface for transmission therethrough, said second surface having a sampling area about one mm or smaller in diameter.

2. The internal reflection element of claim 1 in combination with:
    (b) means adjacent the third surface for adjustably masking off selected portions of the third surface so as to block radiation reflection from a portion of the second surface after transmittal through the third surface, thereby effectively reducing the sampling area at the second surface.

3. The combination of claim 2 including means adjacent to and external to the third surface for moving the masking means from a first position wherein the effective sampling area is about one mm in diameter to a second position wherein the effective sampling area is reduced to about twenty microns in diameter.

4. An internal reflection element for use in spectroscopy comprising:
    (a) an elongated optically-transparent element having at one end a flat first surface for entry of a beam of radiation and having at the opposite end a portion tapering down to a tip to form a flat triangular-shaped sampling second surface and having opposite the sampling surface a flat third surface through which radiation may exit from the element, the element being configured such that radiation entering at the first surface propagates by internal reflection down to the opposite end and becomes incident on the sampling surface at an angle exceeding the critical angle and after reflection from the latter is incident on the third surface at an angle that allows it to exit from the element.

5. An internal reflection element as claimed in claim 4 wherein the element comprises a generally flat elongated element having over most of its length a generally rectangular cross-section and having at said one end an entrance aperture for the beam on its top or bottom surface and a bevelled end opposite said entrance aperture, said element at its opposite end forming a funnel-like portion defining the sampling second surface which extends at an angle to the longitudinal direction of the element, a surface portion of the element opposite the second surface constituting the exit aperture for the beam from the element.

6. The internal reflection element of claim 5 wherein the element has an overall length of about 10 mm and a rectangular cross-section of about $1 \times 1$ mm.

7. An internal reflection element for use in internal reflection spectroscopy comprising an elongated one-piece optically-transparent element having:
   (a) at one end means forming an entrance aperture for a beam of radiation,
   (b) at another end means forming a sampling surface that can be effectively varied in size,
   (c) means forming an exit aperture for a beam of radiation,
   (d) means extending between the ends for guiding without substantial losses a beam entering the entrance aperture toward the sampling surface,
   (e) funnelling means located between the guiding means and the sampling surface for concentrating the guided beam at the sampling surface, and
   (f) means for directing the beam after reflection from the sampling surface toward the exit aperture.

8. An accessory for use with a spectrometer for internal reflection spectrometry comprising the internal reflection element as claimed in claims 1, 4 or 7 in combination with:
   (a) means for transferring a radiation beam from the spectrometer and focussing same at the first surface of the element, and
   (b) means for transferring the modulated radiation beam exiting from the element at its third surface back into the spectrometer for processing.

9. The accessory of claim 8 and further including:
   (c) masking means located adjacent the third surface, and
   (d) means for adjusting the position of the masking means so as to block selected portions of the exiting beam.

10. The internal reflection element of claim 7 in combination with means for selectively masking off the exit aperture to block off radiation from the undesired portions of the sampling surface.

11. A method for conducting examinations of microgram or nanogram quantities of a sample material, comprising the steps:
   (a) introducing a beam of radiation into one end of an elongated internal reflection element over an entrance aperture having a given size,
   (b) guiding the radiation beam in a single pass to the opposite end of the element without any significant dilution,
   (c) concentrating the guided beam when it reaches the opposite end to impinge once on a sampling surface having an effective area smaller than that of the entrance aperture,
   (d) positioning the sample on or near the sampling surface so that the concentrated beam can interact therewith and modulate the beam,
   (e) directing the modulated beam to an exit aperture on the element, and
   (f) processing the exiting modulated beam to form a spectrum containing information about the sample material.

12. The method of claim 11 and including the further step of:
   (g) adjustably masking off the exit aperture to reduce the unmodulated content or undesired portions of the exiting beam before executing step (f).

* * * * *